(12) United States Patent
Martin et al.

(10) Patent No.: US 6,624,097 B2
(45) Date of Patent: Sep. 23, 2003

(54) IMPLANTABLE FIBERS AND MEDICAL ARTICLES

(75) Inventors: Donald H. Martin, Pensacola, FL (US); John H. Southern, Pensacola, FL (US)

(73) Assignee: Solutia Inc., St. Louis, MO (US)

( * ) Notice: Subject to any disclaimer, the term of this patent is extended or adjusted under 35 U.S.C. 154(b) by 124 days.

(21) Appl. No.: 09/730,488

(22) Filed: Dec. 5, 2000

(65) Prior Publication Data

US 2001/0023020 A1 Sep. 20, 2001

Related U.S. Application Data

(62) Division of application No. 08/995,039, filed on Oct. 31, 1997, now Pat. No. 6,162,537.
(60) Provisional application No. 60/030,577, filed on Nov. 12, 1996.

(51) Int. Cl.7 .......................... D02G 3/00; D03D 15/00
(52) U.S. Cl. ...................... 442/199; 428/373; 428/374; 442/200; 606/228; 606/230; 606/231
(58) Field of Search .......................... 428/373, 374, 428/375, 378; 606/228, 230, 231; 442/59, 199, 200

(56) References Cited

U.S. PATENT DOCUMENTS

| | | | |
|---|---|---|---|
| 3,155,754 A | 11/1964 | Adams | 264/78 |
| 3,244,785 A | 4/1966 | Hollandsworth, Jr. | 264/171 |
| 3,251,913 A | 5/1966 | Richards et al. | 264/78 |
| 3,381,074 A | 4/1968 | Bryan et al. | 264/171 |
| 3,458,615 A | 7/1969 | Bragaw et al. | 264/171 |
| 3,463,158 A | 8/1969 | Schmitt et al. | 128/334 |
| 3,613,170 A | 10/1971 | Soda et al. | 18/85 C |
| 3,616,183 A | 10/1971 | Brayford et al. | 161/175 |
| 3,700,544 A | 10/1972 | Matsui | 161/175 |
| 3,797,499 A | 3/1974 | Schneider | 128/334 R |
| 4,075,378 A | 2/1978 | Anton et al. | 428/97 |
| 4,085,182 A | 4/1978 | Kato | 264/171 |
| 4,145,473 A | 3/1979 | Samuelson et al. | 428/373 |
| 4,329,743 A | 5/1982 | Alexander et al. | 3/1 |
| 4,411,027 A | 10/1983 | Alexander et al. | 3/1 |
| 4,512,038 A | 4/1985 | Alexander et al. | 3/1.9 |
| 4,617,235 A | 10/1986 | Shinonome et al. | 428/374 |
| 4,744,365 A | 5/1988 | Kaplan et al. | 128/335.5 |
| 4,756,969 A | 7/1988 | Takeda | 428/372 |
| 4,843,112 A | 6/1989 | Gerhart et al. | 523/114 |
| 4,844,854 A | 7/1989 | Kaplan et al. | 264/235 |
| 4,871,365 A | 10/1989 | Dumican | 623/11 |
| 4,923,470 A | 5/1990 | Dumican | 623/11 |
| 4,942,875 A | 7/1990 | Hlavacek et al. | 606/230 |
| 4,987,665 A | 1/1991 | Dumican et al. | 28/218 |
| 4,990,158 A | 2/1991 | Kaplan et al. | 623/1 |
| 4,997,440 A | 3/1991 | Dumican | 623/1 |
| 5,037,377 A | 8/1991 | Alonso | 600/36 |
| 5,108,424 A | 4/1992 | Hoffman, Jr. et al. | 623/1 |
| 5,123,912 A | 6/1992 | Kaplan et al. | 606/230 |
| 5,124,103 A | 6/1992 | Kaplan et al. | 264/102 |
| 5,197,977 A | 3/1993 | Hoffman, Jr. et al. | 623/1 |
| 5,217,495 A | 6/1993 | Kaplan et al. | 623/13 |
| 5,282,846 A | 2/1994 | Schmitt | 623/1 |
| 5,324,647 A | 6/1994 | Rubens et al. | 435/180 |
| 5,415,619 A | 5/1995 | Lee et al. | 600/36 |
| 5,512,600 A | 4/1996 | Mikos et al. | 521/61 |
| 5,542,594 A | 8/1996 | McKean et al. | 227/178.1 |
| 5,578,046 A | 11/1996 | Liu et al. | 606/151 |
| 5,626,611 A | 5/1997 | Liu et al. | 606/230 |

FOREIGN PATENT DOCUMENTS

| | | |
|---|---|---|
| AU | 28676/89 | 7/1989 |
| EP | 0 202 444 | 11/1986 |
| EP | 0 334 046 | 9/1989 |
| EP | 0 668 083 | 8/1995 |
| NL | 9201035 | 1/1994 |

OTHER PUBLICATIONS

Chu, C.C., "Biodegradable Polymeric Biomaterials: An Overview." In *The Biomedical Engineering Handbook*, J.D. Bronzino et al., eds. (CRC Press), pp. 611–612 (1995).

*Primary Examiner*—Cynthia H. Kelly
*Assistant Examiner*—J. M. Gray
(74) *Attorney, Agent, or Firm*—Hamilton, Brook, Smith & Reynolds, P.C.

(57) ABSTRACT

An implantable medical article as well as an implantable fiber which is particularly useful for medical implants is disclosed. The fiber includes comprises a first component formed from a substantially resorbable material and a second component formed from a fiber-forming polymer.

18 Claims, 9 Drawing Sheets

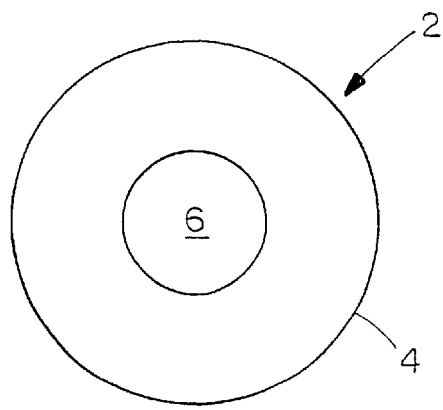
FIG. IA
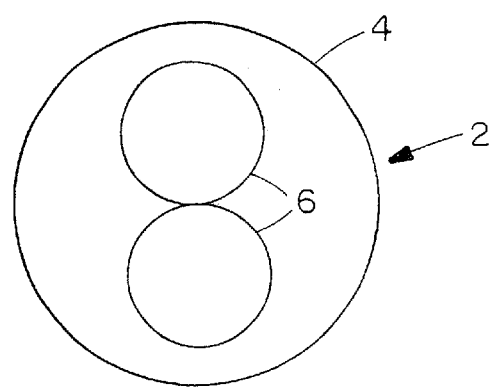
FIG. IB
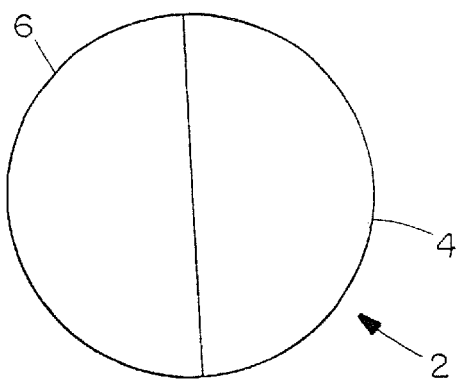
FIG. IC

IMPLANTABLE FIBERS AND MEDICAL ARTICLES

RELATED APPLICATIONS

This application is a divisional of U.S. Application Ser. No. 08/995,039, filed Oct. 31, 1997, now U.S. Pat. No. 6,162,537, which claims the benefit of U.S. Provisional Application No. 60/030,577, filed Nov. 12, 1996. The entire teachings of the above applications are incorporated herein by reference.

FIELD OF THE INVENTION

The present invention relates generally to the field of fibers for use in medical implants and similar in vivo applications. More specifically, the invention relates to fibers for such applications including a first component formed from a resorbable material and a second component formed from a fiber-forming polymer.

BACKGROUND OF THE INVENTION

The practice of medicine and the technology surrounding it continue to evolve in a dramatic fashion. One manifestation of this evolution is the increase in the average human life span which alone spawns the need for still further development, particularly in the area of implantable medical articles, such as in the area of prostheses which either replace or support failing, diseased or deteriorated anatomical parts.

Synthetic materials are known to be useful in the manufacture of many of these implantable articles. Among the more useful synthetic materials in this application are fibers formed from synthetic polymers which are substantially non-resorbable and resistant to degradation in the body. These are often highly desirable for many implantable article applications because of their mechanical properties such as tensile strength, flexibility, and elasticity. Furthermore, their ability to be engineered into useful structures and retain these mechanical properties under the conditions present in the human body can be desirable. For example, certain synthetic fibers formed from polyester have been used in the manufacture of vascular grafts, exhibiting sufficient strength to withstand the pressure of arterial or venous flow while also exhibiting flexibility and recovery. Additionally, fabric vascular grafts possess the versatility to be conveniently implanted into the body without losing structural strength.

For many applications of synthetic polymer fibers in the body, however, the fibers that retain suitable mechanical properties (such as polyethylene terephthalate and polypropylene) do not provide the desired biologic response. Articles formed of these synthetic fibers often have the risk of a negative reaction, for example, chronic inflammation, thrombosis and intimal hyperplasia, sometimes with potentially fatal results.

Fibers made from polymers that can be resorbed by the body (often called "resorbable polymers") can provide a positive and desired biologic response in the body. Examples of such resorbable polymers are polyglycolic acid and polylactic acid and copolymers of glycolic with lactic acid or ε-caprolactone or trimethylene carbonate. In addition to these polyesters are the polyester-ethers such as poly-p-dioxanone.

However, because these polymers are resorbable, the fibers made from them and implanted in the human body typically lose their mechanical properties in a time period considerably shorter than the needed life of an implant. These materials are more typically used as a scaffold for the growth and organization of implanted organ cells. Parenchymal cells are isolated from the desired tissues and seeded into the polymer, and the cell-polymer structure is implanted. While the scaffold gradually deteriorates, the implanted cells proliferate and secrete substances that form an extracellular matrix (ECM). The growing cells, ECM, and vascular tissue continually replace the void spaces of the disappearing scaffold until eventually the implant has been replaced by natural tissue. A spectacular example of this approach is an artificial—but living—human external ear formed on a polymer matrix implanted subcutaneously on the back of a laboratory animal. However, this approach may not be suitable for replacement of tissues that are subject to continuous physical/mechanical demands, such as heart and blood vessel walls, fasciae, ligaments and tendons, bursae and other joint tissues. Therefore, these fibers alone may not be optimal for use in implant applications.

Thus a major problem is inherently present in implantable prosthetic articles that are formed from materials such as synthetic fibers because of the prior art fibers' inability to both retain good long term mechanical properties and also elicit a positive and desirable biologic response. One particular area in which this combination of desired properties has not been achieved is in the use of small bore (~6 mm diameter) vascular grafts. Availability of suitable small diameter vascular grafts could significantly expand the opportunities for vascular repair since arteries having diameters in this range, such as the radial artery and the arteries in the Circle of Willis, provide a major component of the blood supply to key organs and extremities and are often in need of repair due to injury or disease.

It is also known from Poiseuille's Law that flow through blood vessels is proportional to the fourth power of the vessel radius. Reducing the diameter of a blood vessel by half, as may occur in intimal hyperplasia or partial thrombosis, reduces the vessel's blood flow to 1/16th the original flow. Due to the small size and, in general, low blood flow, these small grafts put an even greater demand on maintaining a clear cross-sectional area for blood flow. Unfortunately, there are currently no synthetic vascular grafts that work well in this application. This is a severe problem and one for which a truly workable fiber and vascular graft fabric would be a major step forward.

Prior attempts to provide fibers with both long term mechanical properties and biocompatibility have been largely unsuccessful. One approach has been to use resorbable fibers and biologically stable fibers such as those described above together in an implantable fabric such as a vascular graft. This approach is described, for example, in EPO Application 0 202 444 (Nov. 26, 1986) and U.S. Pat. No. 4,997,440 (Mar. 5, 1991).

However, published results have shown that these types of constructions fail because even a modest amount (20%) of the non-resorbable polymer fibers exposed and present inside the body (in this case polyethylene terephthalate) significantly inhibited the desired biologic response (*J. Vasc. Surgery*, 3(5), May 1986). Furthermore, experimental results indicate that even at nominal levels of the non-resorbable component, problems of fabric failure and/or defects leading to potential aneurysm still exist as indicated in U.S. Pat. No. 4,997,440 which indicates from "slight" to "significant" aneurysmal tendency in grafts with 25% to 33% non-resorbable fiber.

Another approach to address these limitations has been to coat the prosthetic fabric. For example, EPO Application 334 046 discloses a surgical composite which is manufactured by extruding a non-resorbable polymer into a fiber, fabricating the fiber into a textile structure and then encapsulating the structure with a resorbable polymer. Such an approach has several drawbacks including changing the relative flexibility of the basic fabric graft. Additionally, by virtue of the coating process, the resulting fabric is less likely to have the small open pores and interstitial channels which are useful for cell and tissue ingrowth from outside the graft through the wall into the vessel lumen. Further, such coating processes do not reliably provide a desirable uniform coating layer on individual filaments with controlled thickness of the coating layer.

A continuing need therefore still exists for a practical and economically manufacturable, useable implantable prosthetic article which exhibits the properties necessary to perform the desired function for the prosthetic within the body while maintaining its structural and functional integrity and performance and bringing about a positive biologic response leading to healing and the desired functioning of the prosthesis.

SUMMARY OF THE INVENTION

The present invention meets this need and also achieves the other desirable results discussed below by providing an implantable medical article (for example, sterile medical articles) as well as an implantable fiber which is particularly useful for medical implants.

The fiber of this invention comprises a first component formed from a substantially resorbable material and a second component formed from a fiber-forming polymer.

In particular, a bicomponent fiber of the invention comprises a first polymer component formed from a substantially resorbable material and a second component formed from a fiber-forming polymer wherein the volume ratio of said first component and second component is substantially the same along the length of the fiber. In another embodiment, the bicomponent fiber of the invention comprises a first component formed from a substantially resorbable material and a second component formed from a fiber-forming polymer wherein the melting point of the second component is substantially the same as or less than the melting point of the first component. In a third embodiment of the invention, the bicomponent fiber comprises a first component formed from a substantially resorbable material and a second component formed from a fiber-forming polymer wherein said first component is substantially free of cracks or delamination. The invention also includes bicomponent fibers comprising a first component formed from a substantially resorbable material and a second component formed from a fiber-forming polymer wherein said first component possesses a substantially uniform thickness along the axis of the fiber. In yet another embodiment, the fiber is characterized by a first polymer component formed from a substantially resorbable material and a second polymer component manufactured from a fiber-forming polymer wherein both the first and second components are substantially oriented. In a preferred embodiment, the bicomponent fiber is characterized by a first substantially resorbable component and second fiber-forming polymer component wherein said first and second component both contribute to the tenacity of the bicomponent fiber. In a preferred embodiment the bicomponent fiber contains two or more (including all) of the above described characteristics in any combination. In a more preferred embodiment the fibers, as are described herein, are characterized by said second component being substantially disposed within said first component, as in a sheath/core configuration. Alternatively, the two components of the fiber are configured adjacent and parallel to each other along the length of the fiber.

The invention also includes methods of manufacturing bicomponent fibers, particularly by solution wet spinning, melt spinning and solution dry spinning processes, as well as methods of using the bicomponent fibers, for example, in the manufacture of implantable fabrics (such as, knitted, braided and woven fabrics comprising one or more of the bicomponent fibers) and prosthetic devices and methods of using the bicomponent fibers and implantable fabrics made therefrom in vivo.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 1A, 1B and 1C are elevated cross-sectional views of separate embodiments of the present implantable fiber.

DETAILED DESCRIPTION OF THE INVENTION

Figure 2:
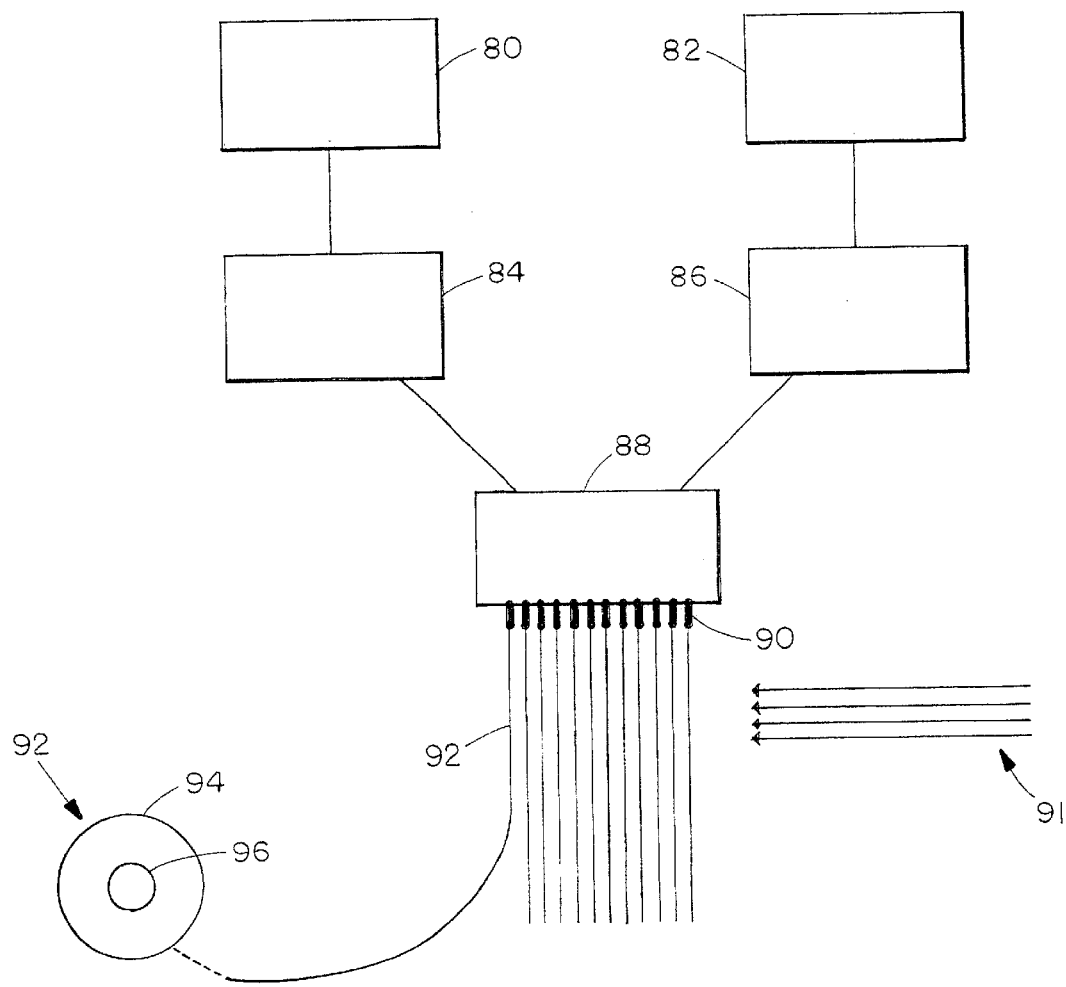
FIG. 2 is a schematic illustration of melt spinning process for forming the fibers with an exploded cross-sectional view of a singular fiber.

The term "fiber", as utilized herein, is defined to include continuous filaments, staple fibers formed therefrom and monofilament or multifilament fibers.

As utilized herein, "bicomponent fibers" are fibers formed from 2 or more components, each of which is distinct and discernable, i.e. not blended together.

The term "yarn" as utilized herein, is defined as a strand of fibers and can be made from one or more bicomponent fibers (which can be the same or different) of the invention, optionally, in combination with one or more other fibers (e.g., not bicomponent fibers as described herein).

The term "polymer", as utilized herein, is defined to include homopolymers, copolymers, terpolymers and the like as well as polymer blends.

The term "biopositive", as utilized herein, is defined as having the capability, or property, of allowing and/or eliciting a positive biologic response in the human body over time. Examples of positive biologic responses include (but are not limited to) desirable growth factor and cytokine stimulation, cellular migration and proliferation and tissue regeneration. It would be understood by one of ordinary skill in the art that whether or not a certain biologic response is positive may depend on a number of factors, including, for example, the particular application or desired function of the implantable article or implantable fiber. In the case of an implantable fabric, such as an arterial graft, a biopositive polymer can be a polymer which, when employed as the sheath of a bicomponent fiber, will degrade in vivo over time, the polymer or degradation products thereof, stimulating cellular migration and/or tissue generation from outside the fabric or graft through the fabric or graft and into the vessel lumen. Tissue ingrowth can be promoted by enhanced porosity produced by the resorption of the component(s) of the bicomponent fiber. The biopositivity of the fiber or component thereof can be imparted by the nature of the component or can be imparted by the presence of an additive to the component, as will be described in more detail below.

The term "resorbable material" as utilized herein, is defined as a material which is capable of being disassembled from its original molecular form by the human body and optionally eliminated from the human body by one or more mechanisms within the human body (for example, typically within one year of implantation). Polyglycolide polymers, such as polyglycolic acid (PGA) and polylactide/polyglycolide copolymers (PLGA), for example, are hydrolyzed in vivo into soluble monomers and/or soluble oligomers and, thus, eliminated.

FIGS. 1A, 1B and 1C illustrate cross-sections of two embodiments of the implantable fiber 2 of the present invention. The fiber in FIG. 1A has a first component 4 and a second component 6. The first component is formed from a substantially resorbable material. The second component of the fibers of the present invention is preferably substantially disposed within the first component. As illustrated, the second component is substantially concentrically disposed within the first component. Thus, the second component can also be disposed in a non-concentric orientation. FIG. 1B illustrates a bicomponent fiber comprising a first component 4 formed from a substantially resorbable material and two second components (which can be the same or different) 6 which are disposed within the first component. FIG. 1C illustrates a bicomponent fiber wherein the first and second component are each exposed to the exterior of the fiber. It will be understood by one of ordinary skill in the art that the specific disposition of the two components will depend on a variety of factors, including for example the application/utility of the fiber.

In general, the ratio of the first component to the second component may be substantially the same for all fibers in an article which includes such fibers. However, there may be some applications in which one would desire to have some fibers with a relatively thinner first component which could be resorbed by the body in a relatively short time period and other fibers with a relatively thicker first component which could be resorbed over a relatively longer time period.

The choice of the volume ratio of first component to second component will, in general, range from about 1:10 to about 10:1 with the specific choice depending upon the particular fiber application. More preferably the volume ratio of the first component to second component will vary from about 1:3 to about 3:1. Such control of the ratio of first component to second component for each and every fiber is within the scope and capability of the spinning techniques described in this invention and known in the art. Preferably, the ratio of the first component to the second component is substantially constant along the length of the fiber.

The volume ratio of the components of the fiber can be calculated by determining the surface area of each component in a cross-section of the fiber and dividing the value obtained from the first component by the value obtained by the second component. By "substantially the same", it is meant that at least about 90% (preferably at least about 95% and more preferably at least about 99%) of a statistically significant number of volume ratios taken across the length of the fiber (e.g. a meter or more) vary in an amount less than 10%. It is particularly preferred that the first component (or the sheath of the fiber) be substantially free of cracking or delamination.

Similarly, the geometric distribution of the second and first polymer are preferably substantially the same along the length of the fiber. For example, the thickness of the one or both components is substantially uniform along the length or axis of the fiber. Additionally or alternatively, the volume, volume fraction, or cross-sectional surface area of one or both (preferably both) are substantially constant along the length of the fiber. Thus, the preferred bicomponent fibers of the invention are essentially uniform along the length of the fibers.

A broad class of substantially resorbable materials suitable for the first component of the fibers of the present invention include natural and synthetic substantially resorbable polymers such as those described in the *Biomedical Engineering Handbook*, p. 612, (1995), which is incorporated herein by reference. Examples of these substantially resorbable polymers include polyglycolides, polydioxanones, polyhydroxyalkanoates, polylactides, alginates, collagens, chitosans, polyalkylene oxalate, polyanhydrides, poly(glycolide-co-trimethylene carbonate), polyesteramides, polydepsipeptides and the like. More specifically, substantially resorbable polymers include polyglycolic acid and polylactic acid, and copolymers of glycolic acid with lactic acid or ε-caprolactone or trimethylene carbonate. In addition to these polyesters are the polyester-ethers such as poly-p-dioxanone.

Polyglycolides are particularly suitable polymers for the first component as they are resorbed at a rate that corresponds to the typical healing rate of the human body. However, it can be understood by one of ordinary skill in the art that selection of the preferred polymer for the first component will depend on a number of factors, including for example the particular application or desired function of the implantable article or implantable fiber and the desired resorption rate for the first component in that application. The molecular weight of the polymer is not particularly critical. However, examples of polyglycolides include polymers possessing a molecular weight of at least about 2000 daltons, for example. The ratio of glycolic acid and lactic acid in a suitable polyglycolide can also vary widely, depending, for example, on the desired rate of degradation in vivo, as is generally known in the art.

Most preferably, the first component is biopositive. In a first preferred embodiment, the first component is formed from a resorbable material which is itself biopositive by virtue of its composition or structure. Examples of such polymers include certain resorbable polymers such as polyglycolic acid and polylactic acid, copolymers of glycolic acid with lactic acid or ε-caprolactone or trimethylene carbonate. In addition to these polyesters are the polyester-ethers such as poly-p-dioxanone. In a second preferred embodiment, the first component is formed from a resorbable material which further includes at least one additive which renders the first component biopositive. Such would be the case, for example, with a polymer having incorporated therein or added or applied thereto additives such as heparin or other materials which impart biopositivity.

In a preferred embodiment, the first component can also be fiber-forming, as that term is normally employed in the art, under the conditions of manufacture of the fiber. In such an embodiment, the first component of the bicomponent fiber can contribute to the tenacity of the fiber and/or can be substantially or highly oriented.

The polymer used to form the second component 6 of the fiber 2 may be any known fiber-forming natural or synthetic polymer such as, for example, a polyester, polyamide, polyolefin, polyurethane, polyester/polyether block copolymers or other composition which brings to the final fiber desired mechanical properties, alone and/or together with the first component. Particular examples of such polymers include polypropylene, polyethylene, polybutyleneterephthalate and polyhexyleneterephthalate and copolymers thereof. In one embodiment, the second component can be a polymer characterized by the ability to form a fiber at a temperature of at least about 120° C., preferably, at least about 150° C. In another embodiment, the second component, together with the first component, is substantially oriented. In one preferred embodiment of the invention, it has been found that bicomponent fibers can be formed from polymers, employed as the first and/or second component, which can withstand or sustain high temperatures during fiber formation while maintaining or achieving good to superior mechanical integrity of the fiber.

Preferably, the polymer is not substantially resorbable; however, it is to be understood by one of ordinary skill in the art that polymers which meet the definition of the term resorbable material as utilized herein may be utilized for the second component 6 (FIGS. 1A–1C). Should a resorbable polymer be utilized in the second component 6, it is preferred that such a polymer have a rate or resorption different than, most preferably slower than, that of the resorbable material for the first component.

As above, the molecular weight of the fiber-forming polymer of the second component is not critical to the invention. The molecular weight is generally sufficient to form a fiber in, for example, monocomponent melt spinning. Examples of suitable polyesters can possess a molecular weight of at least about 15,000 daltons or at least about 20,000 daltons. Where a polyolefin is selected, the molecular weight can be at least about 60,000 daltons or at least about 70,000 daltons or, preferably, at least about 100,000 daltons.

In one embodiment of the invention, the second component of the fiber is a polymer possessing a melting point which is substantially the same or less than the melting point of said first component. Where the first component is a polyglycolide (such as PGA or PLGA) and the second component is a polyester, the melting point of the polyester second component can be greater than about 100° C. Likewise, where the first component is a polyglycolide and the second component is a polyolefin, the melting point of the polyolefin can be greater than about 100° C.

In an embodiment of the present invention, at least one of the components 4 or 6, or both components 4 and 6, further include at least one additional ingredient, such as a pigment or pharmaceutically active agent, which may be, for example, applied to the fiber or components thereof and/or incorporated within the polymer. In a preferred embodiment of FIG. 1A, at least the first component 4 includes a pigment or pharmaceutically active agent. The pharmaceutically active agent may be the same as or different from an additive described above which imparts biopositivity to the first component (such as, heparin). The incorporation of pharmaceutically active agents may be desired to augment the local healing response to the fiber or to provide local or systemic delivery of agents which improve device performance and clinical outcome. For example, in the embodiment wherein the implantable article of the present invention is useful in vascular graft applications, the pharmaceutically active agents could include therapeutic targets involving coagulation events, hyperplasia and hypertrophic tissue response, downstream vascular patency and flow, and infection. Nonvascular applications for the fiber/implantable article can benefit from an entirely different tissue response than vascular application and these could be mediated by a combination of active agent and polymer.

Particularly useful agents include:

1) thrombosis inhibitors such as: inhibitors of enzymes in the intrinsic or extrinsic coagulation cascade such as heparin, hirudin, or tick anticoagulant peptide, antiplatelet agents such as inhibitors of glycoprotein IIb/IIIa or the prostacyclin analogs, 2) fibrinolytics such as tissue plasminogen activator, streptokinase and urokinase, 3) vasodilator substances such as prostacyclin and nitric oxide donor molecules, 4) anti-inflammatory agents such as the steroids and nonsteroidal drugs, 5) cell proliferation inhibitors such as c-myb and c-myc antisense oligonucleotides and mitosis inhibitors, 6) inhibitors of matrix elaboration or expression such as collagen antisense nucleotides or amino acid analogs which inhibit collagen gelation such as beta-aminopropionitrile or halofunginone, 7) inhibitors of cell migration such as RGD peptides or peptide or peptidomimetic antagonists of integrins, 8) promoters of endothelial cell proliferation such as the vascular endothelial growth factors, acidic fibroblast growth factors and basic fibroblast growth factors, and 9) promoters of osteogenesis and chrondogenesis such as members of the TGFβ superfamily or members of the bone morphogenetic protein family.

It should also be understood that one or both components can include other additives as well. For example, pigments, dyes, stabilizers, antioxidants, and/or antiozonates can be added to one or both polymer components. Preferably, the additive is pharmaceutically acceptable, as is known in the art. The additives can improve stability during fabric processing conditions and/or fiber properties in the body. It will be understood by one of ordinary skill in the art that the types and amounts of these additives can depend upon different factors such as the temperatures of processing, the environmental conditions to which the fibers are exposed during fabrication into medical devices, storage and eventually upon the environment to which the fibers are exposed in the body.

In other embodiments, natural or genetically altered cells from human or other sources are alternatively or additionally attached to or incorporated into the fiber structures to seed the implant article with cells that, upon multiplication and/or differentiation in the implant, impart desired biopositive or physiological characteristics to the implant.

It should be understood by one of ordinary skill in the art that the nature and type of the pharmaceutically active agent should be selected based on the particular application/utility or desired function of the implantable device or implantable fiber. For example, a fibrous mesh of this invention seeded with human allograft or autograft beta cells can be implanted to create an artificial insulin-secreting gland following total pancreatectomy. Such cells can be present alone or in combination with pharmaceutically active agents.

In an embodiment wherein both components 4 and 6 include a pharmaceutical agent or living cells, the pharmaceutical agent or cells of component 4 may be the same as or different from the pharmaceutical agent of component 6. The pharmaceutical agent may be added or applied after the fiber is formed or may be incorporated into the polymer matrix prior to formation of fiber.

In a preferred embodiment, shown in FIG. 1A, the bicomponent fiber of the present invention is a single filament. In this embodiment, the first component 4 and second component 6 are preferably formed simultaneously which results in several advantages such as the ability to control the ratio of first component to second component along the length of the fiber as well as amongst fibers in an article which includes such fibers.

Fibers of the present invention are preferably formed by any of several different methods generally known in the art which result in the simultaneous formation of first component and a second component. Such processes are exemplified in the references noted in the publication *Bicomponent Fibers A Review of the Literature*, Textile Research Institute, Report No. 44, (1993) which is herein incorporated by reference. Examples of processes which can be modified to manufacture bicomponent fibers of the present invention include melt spinning, solution wet spinning and solution dry spinning, each of which will be discussed in more detail below.

In each of the examples and processes described below, the first component is formed from a substantially resorbable material which is a substantially biopositive, resorbable polymer and the second component is formed from a fiber-forming polymer which is not substantially resorbable. Thus, the invention includes a method for manufacturing an implantable bicomponent fiber comprising simultaneously melt-extruding from a spinnerette in a sheath-core filament configuration, a first polymer component formed from a substantially resorbable material and a second component formed from a fiber-forming polymer.

In another embodiment, the invention includes a method for manufacturing an implantable bicomponent fiber comprising (a) simultaneously solution-spinning from a spinnerette in a sheath-core filament configuration, a first solution comprising a first solvent and a first polymer component formed from a substantially resorbable material and a second solution comprising a second solvent and a second component formed from a fiber-forming polymer, thereby forming a prefilament and (b) removing substantially all of said first and second solvents from said prefilament thereby forming a bicomponent fiber wherein said second component is substantially disposed within said first component. In particular, the first and second solvents are removed by extraction with a coagulation liquid or by evaporation.

FIG. 2 discloses one embodiment of a method for forming a fiber of the present invention as depicted in FIG. 1A via a melt spinning process. In FIG. 2, resorbable polymer 80 and fiber-forming polymer 82 are melted and simultaneously extruded through melt extruders 84 and 86 respectively. Polymers 80 and 82 are extruded through a spinnerette 88 via spinning capillaries 90 to form streams which are cooled, typically by gaseous crossflow 91, to form fibers 92 having first components 94 formed of polymer 80 and second components 96 formed of polymer 82. The melt temperatures and extrusion conditions are dictated by several factors such as the melt and degradation temperatures and viscosity of resorbable polymer 80 and fiber-forming polymer 82, and the characteristics of extruders 84 and 86, spinnerette 88 and spinning capillaries 90 used to produce fiber 92 having first component 94 formed from a resorbable polymer and second component 96 formed from a fiber-forming polymer. In a melt formation process the more common polymers used have melting point ranges from polyethylene (with a melting point of about 115° C.) to nylon 6,6 and polyethylene terephthalate (with melting points of about 260° C.). A preferred polymer pair for this process are polyglycolic acid for the resorbable material and polypropylene for the fiber-forming polymer.

Figure 3:
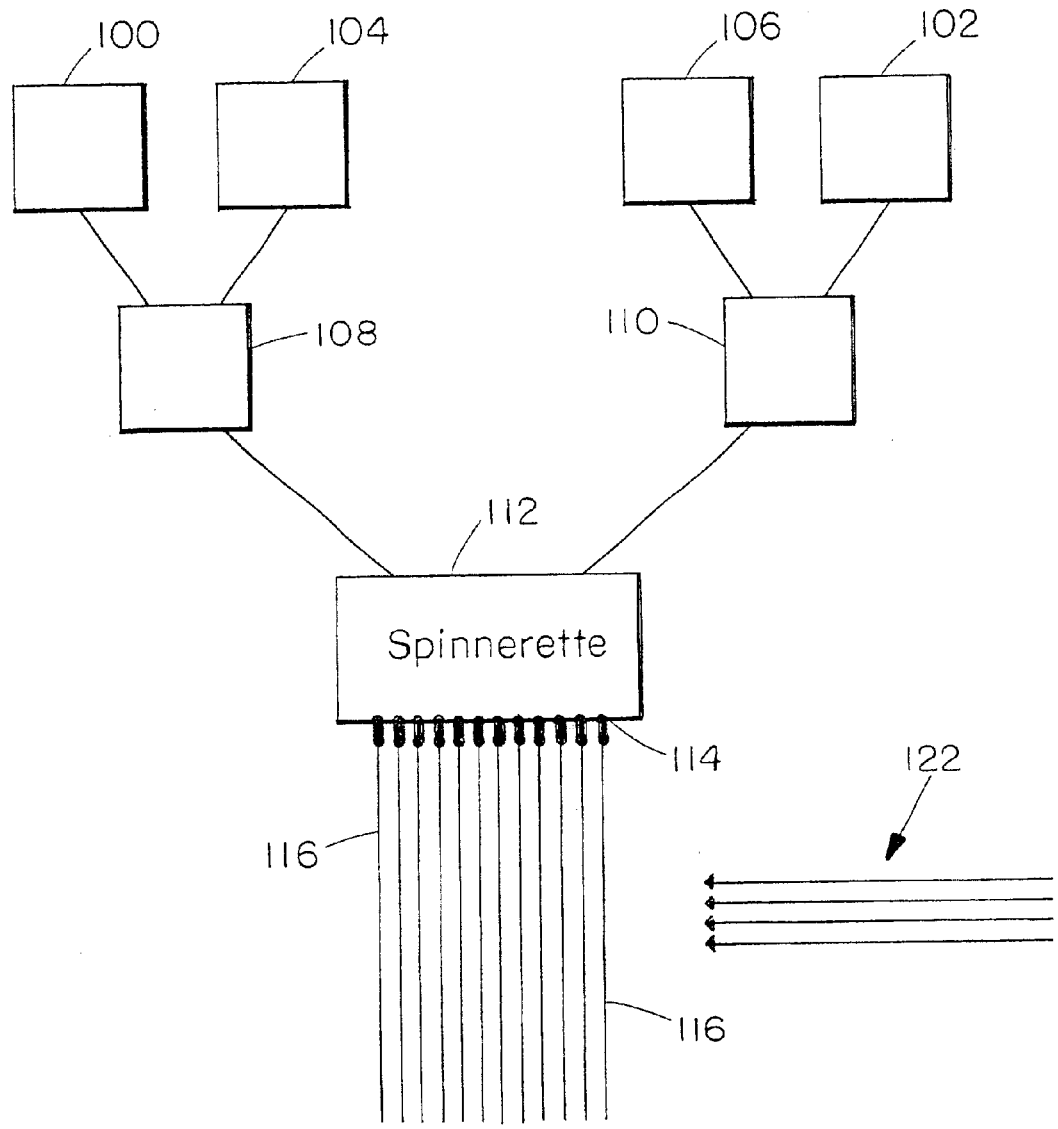
FIG. 3 is a schematic illustration of a solution dry spinning process for forming the present fibers with an exploded cross-sectional view of a singular fiber.

FIG. 3 discloses one embodiment of a method of forming a fiber of the present invention as depicted in FIG. 1A via a solution dry spinning process. In FIG. 3, resorbable polymer 100 and fiber-forming polymer 102 are dissolved in appropriate solvent(s) 104 and/or 106. The selection of the solvent depends upon the type of polymer and can differ for resorbable polymer 100 and fiber-forming polymer 102. Examples of solvents include water, acetone, dimethylformamide, dimethyl acetamide, methyl ethyl ketone, chloroform, methylene chloride, ethyl acetate, n-butanol and the like. The solvent/polymer mixtures 108 and 110 are extruded through spinnerette 112 and spinning capillaries 114 to form fibers 116. The solvent(s) 104 and/or 106 are generally evaporated from the extruded components 118 and 120 by a gaseous cross flow (e.g., hot gas) 122 (usually air or $N_2$). An example of a fiber that would be preferably made by this process would be one in which the resorbable polymer is not "meltable" such as the alginates, chitosans or amino acid polymers. Preferred choices for the fiber-forming polymer for this process would be polyesters, polyamides, polyolefins, polyurethanes or polyester-polyether block copolymers or their chemically modified (for solubility characteristics) derivatives.

Figure 4:
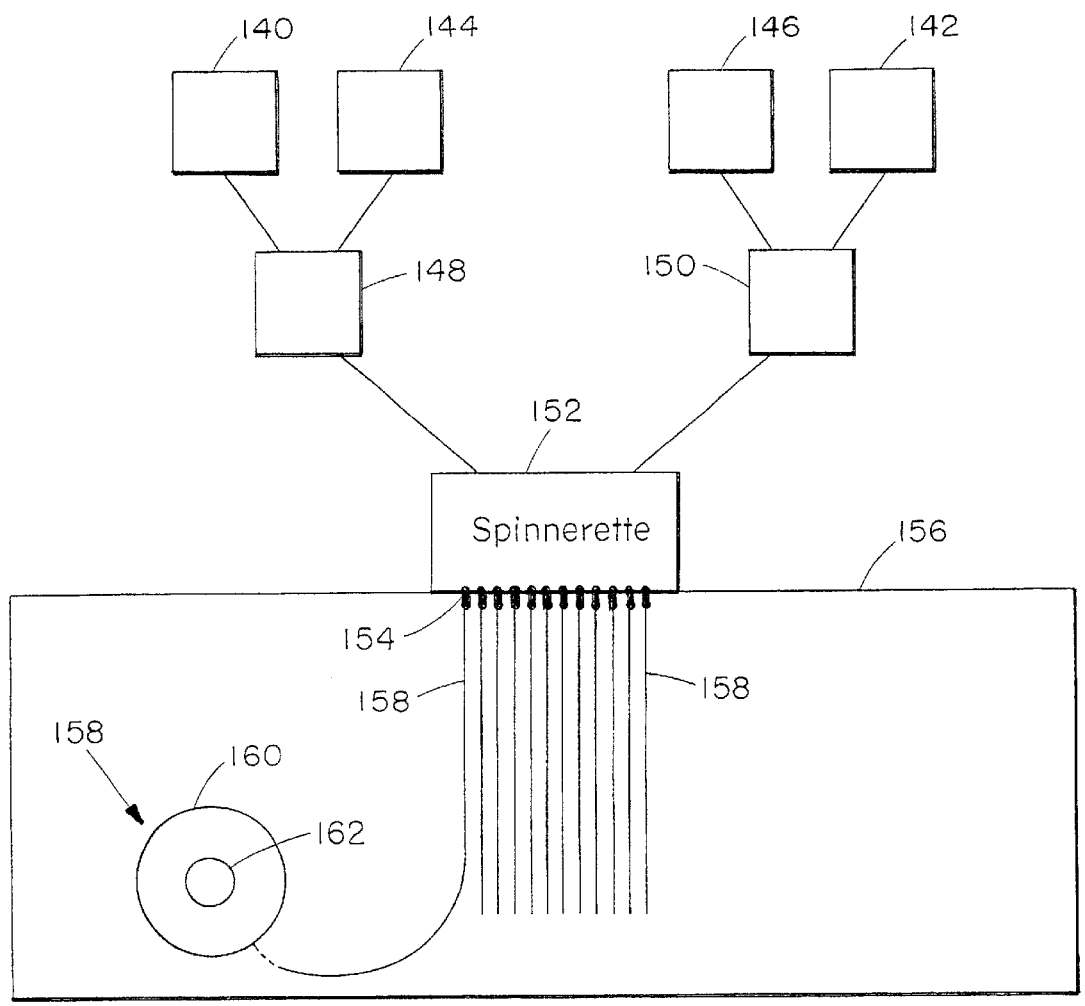
FIG. 4 is a schematic illustration of a solution wet spinning formation process with a wet jet for forming the present fibers with an exploded cross-sectional view of a singular fiber.

FIG. 4 discloses one embodiment of a method of forming a fiber of the present invention as depicted in FIG. 1A via a solution wet spinning process with a wet jet. In FIG. 4, resorbable polymer 140 and fiber-forming polymer 142 are dissolved in appropriate solvent(s) 144 and/or 146. The selection of the solvent depends upon the type of polymer and may differ for resorbable polymer 140 and fiber-forming polymer 142. Examples of solvents include water, acetone, methyl ethyl ketone, dimethylformamide, dimethyl acetamide, n-butanol and the like. The solvent/polymer mixtures 148 and 150 are extruded through spinnerette 152 and spinning capillaries 154, directly into a coagulation bath 156 which is filled with a coagulation liquid, typically a mixture of a solvent and water or any appropriate combination of miscible or immiscible solvent(s) and non-solvent(s). This process forms fibers 158 having first components 160 formed of resorbable polymer 140 and second components 162 formed of fiber-forming polymer 142. An example of a fiber that would be usefully made by this process would be one in which the resorbable polymer is not meltable such as the hyaluronic acids, their esters and deacetylated hyaluronic acid derivatives, alginates, chitosans or amino acid polymers. Preferred choices for the fiber-forming polymer for this process would be polyesters, polyamides, polyolefins, polyurethanes or polyester-polyester block copolymers or their chemically modified (for solubility characteristics) derivatives.

Figure 5:
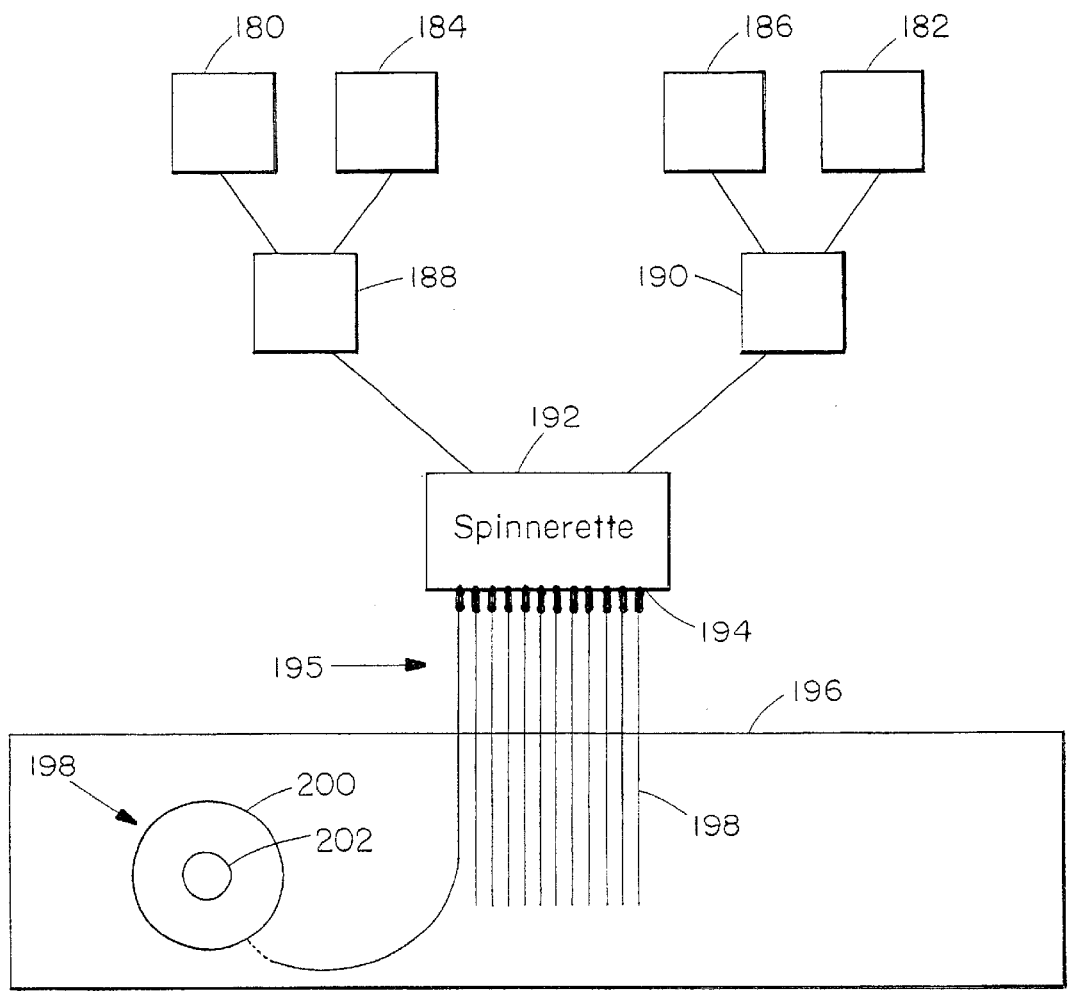
FIG. 5 is a schematic illustration of a solution wet spinning formation process with a dry jet for forming the present fibers with an exploded cross-sectional view of a singular fiber.

FIG. 5 discloses one embodiment of a method of forming a fiber of the present invention via a solution wet spinning process with a dry jet. In FIG. 5, resorbable polymer 180 and fiber-forming polymer 182 are dissolved in appropriate solvent(s) 184 and/or 186. The selection of the solvent depends upon the type of polymer and may differ for resorbable polymer 180 and fiber-forming polymer 182. Examples of solvents include acetone, dimethylformamide, dimethyl acetamide, n-butanol and the like. The solvent/polymer mixtures 188 and 190 are extruded through spinnerette 192 and spinning capillaries 194, through a gap 195, usually air, into a coagulation bath 196 which is filled with a coagulation liquid, typically a mixture of a solvent and water. This process forms fibers 198 having a first component 200 formed of resorbable polymer 180 and a second component 202 formed of a fiber-forming polymer 182. An example of a fiber that would be usefully made by this process would be one in which the resorbable polymer is not meltable such as the hyaluronic acids, their esters and deacetylated hyaluronic acid derivatives, alginates, chitosans or aminoacids polymers. Preferred choices for the fiber-forming polymer for this process would be polyesters, polyamides, polyolefins, polyurethanes or polyester-polyether block copolymers or their chemically modified (for solubility characteristics) derivatives.

The solution formation processes shown in FIGS. 3–5 and discussed above may be carried out at moderate or room temperatures (15° C. to 35° C.). Room temperature (or close to room temperature) processing allows the use of a wide variety of additives and/or drugs which might decompose or degrade at elevated temperatures. In the solution formation processes shown in FIGS. 4 and 5, the resorbable polymer and the fiber-forming polymer may be matched with the polymers' respective solvents. Suitable solvents may be selected from a class of more "biofriendly" solvents, or solvents which can be employed in the manufacture of pharmaceutical products, for example water, n-butanol, tetrahydrofuran (THF), n-methylpyrrolidone (NMP) or ethylacetate, so that any trace residuals remaining within the fiber, particularly the first component of the fiber, do not adversely react with the body at that concentration.

Although it is preferable as discussed above that the first component and the second component be simultaneously formed in this embodiment, it is to be understood that other processes that result in sequential formation of the first and second components are within the scope of the invention. For example, the first component may be applied as a coating via conventional coating processes such as dip coating (e.g., through a solution comprising the first polymer component and a suitable solvent) or plasma coating to the second component after the second component is formed via conventional filament spinning processes.

In any event, as discussed above, the process selected will depend largely upon the properties of the first and second component (the relative melting points and degradation temperatures, the solubilities, and the presence of one or more additives, for example).

In a second embodiment, shown in FIG. 1B, the fiber of the present invention is a multifilament fiber wherein the second component 6 includes a plurality of individual filaments 10. In this embodiment, first component 4 is preferably applied as a coating to the second component after the second component is formed via conventional filament spinning processes.

Figure 6:
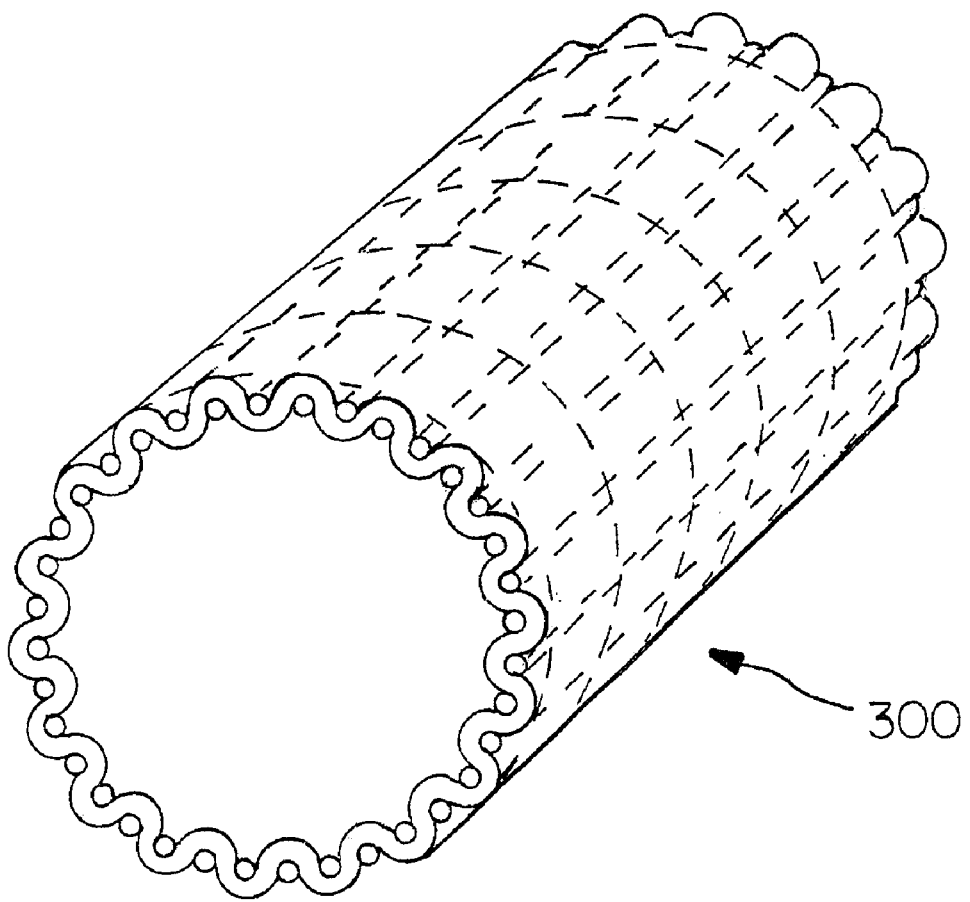
FIG. 6 is an elevational view, partially in cross-section, of an implantable article of the present invention, more particularly a vascular graft.
Figure 7A:
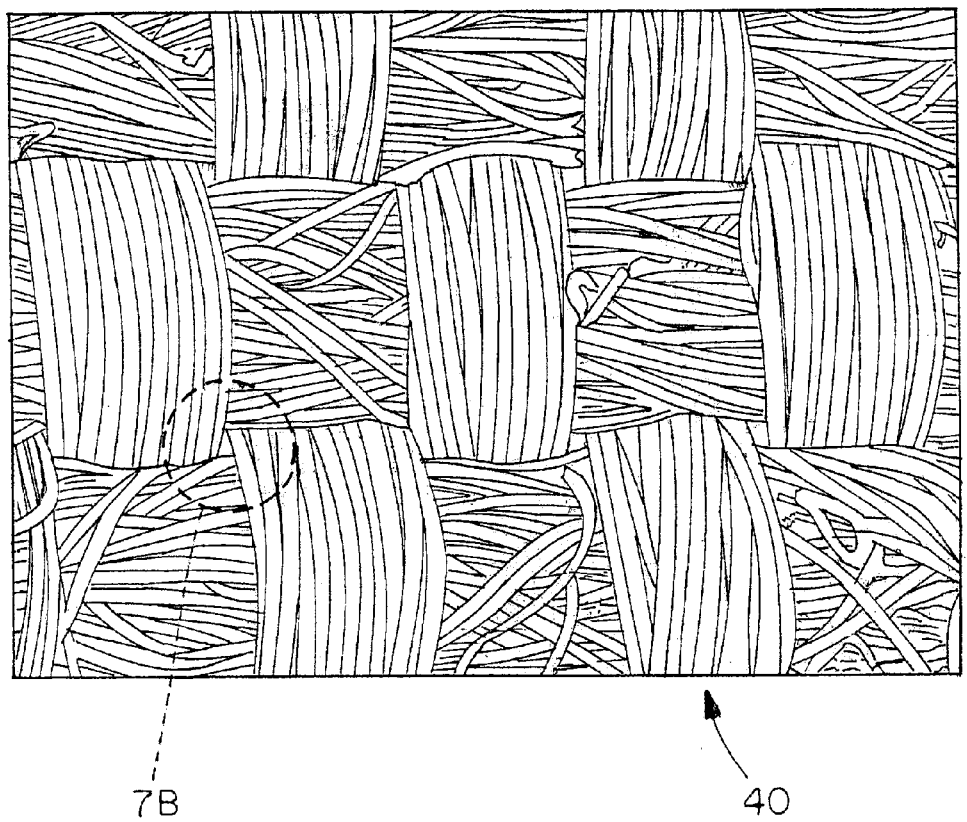
FIG. 7A is a top view of a portion of an embodiment of a textile based structure useful in the implantable article of the present invention.
Figure 7B:
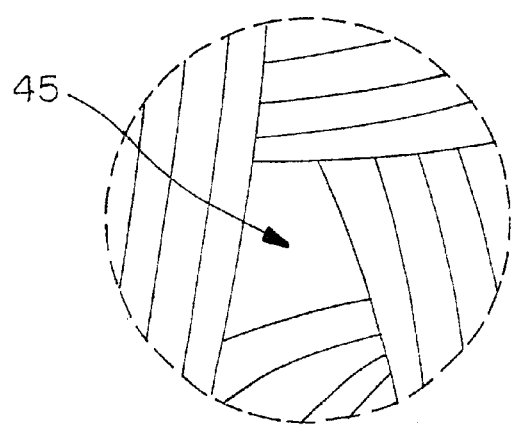
FIG. 7B is a partially exploded portion of FIG. 7A.

The implantable fibers of the present invention are particularly useful in applications relating to implantable medical articles 300, particularly sterile, implantable medical articles, such as the vascular graft depicted in FIG. 6 which include a textile-based structure 40 as depicted in FIG. 7. Preferred textile-based structures include a plurality of fibers with at least one of the fibers being an implantable bicomponent fiber of the present invention. Non-limiting examples of textile-based structures include fabrics, cloths, webs or similar structures which can have, for example, woven, knitted, braided or non-woven constructions. Textile-based structures may contain a single fiber of the present invention or a plurality of fibers of the present invention. As such, it is preferred that the fibers of the invention possess sufficient mechanical properties (including, for example, tensile strength, flexibility, creep and elongation properties) to permit manufacture of textiles suitable for implantation. For example, it is desirable that the fiber have sufficient tensile strength as to avoid breakage during commercial weaving and or knitting. Generally, a fiber characterized by a filament diameter of about 15 microns is preferably characterized by a tensile strength of at least about 1.5 grams per denier, preferably at least about 3.5 grams per denier. Elongation is generally preferred to be less than 65% at conditions of use.

Textile-based structures and processes for their formation are well known in the art as exemplified and described in textbooks such as *Textiles* by N. Hollen and J. Saddler, The MacMillan Company (1973). In forming the textile structures useful in these applications, it is to be understood that, depending on the specific utility of the implantable article, the textile structure may include the fibers of the present invention, yarns formed from the fibers of the present invention or a combination thereof, as well as other implantable synthetic polymer fibers already known to the art. For textile-based structures which include fibers of the present invention or yarns formed therefrom, it is preferred that the textile-based structure include interstices 45 (FIG. 7) along the structure.

Examples of such implantable medical articles include prosthetics such as vascular grafts, stents, artificial replacement ligaments, implantable soft tissue prostheses such as breast and penile prostheses; cartilage replacement prostheses for the joints, nose and ear; implantable support meshes; hernia implant fabrics; AV shunts; tympanoplasty patches; atrial, ventricular, septal and pericardial patches; endarterectomy patches and the like. Other examples include suture cuffs and tags and other exterior structures for medical implants, such as implantable heart valves, including artificial valves and natural hetero- and homo-graft valves; intracranial pressure relief valves; implantable pacemakers and defibrillators; implantable monitors and drug delivery pumps; and the like.

It will be understood by one of ordinary skill in the art that the fibers of the present invention should not include any material or component which would induce an unacceptable toxic, cytotoxic or immunogenic response once implanted as part of these or other implantable articles.

While the present invention has been described with detail and with specific references to preferred embodiments, it is to be understood that many variations of the present invention which do not depart from its spirit and scope may be made. For example, the fibers of the present invention may further include one or more outer coatings on the surface thereof, including cell coatings, which may improve their implantability or performance. Also, the polymer utilized for the second component may also be a resorbable material as that term is defined and may have resorption characteristics different from those of the resorbable material utilized for the first component. For example, the first component may be formed from a first resorbable material and the second component may be formed from a polymer which is a second resorbable material the first and second resorbable materials have differential resorption rates. Implantable articles formed therefrom would be of a temporary nature or used in applications where their useful life is relatively short. Further, the articles of the present invention may be used in conjunction with other implantable articles comprising other implantable materials, including without limitation implantable synthetic polymers in fiber, sheet or solid structural form; metals such as stainless steel and vitallium; and other biocompatible materials such as ceramics, pyrolytic carbons, hydroxyapatites and the like.

EXPERIMENTAL

General Process Descriptions

1) Two Step Spin and Draw Process

Referring to FIG. 2, the core materials 82, polypropylene (PP, Aristech Chemical Corporation—F040A extrusion grade for sutures, nominal melt flow index of 4)) or polybutyleneterephthalate (PBT, Entec Polymers-Celanex 1600A (unfilled and low flow) and Celanex 2002-3 (unfilled and medium flow), were dried to remove any residual moisture. The sheath material 80 (resorbable polymer like polyglycolic acid (PGA, Brimingham Polymers, Inc., homopolymer polyglocolic acid—inherent viscosity (measured at 30° C. in hexafluoroisopropanol) 1.54 dl/g)) was dried under vacuum to a moisture level of below 0.005%. These materials were fed into the extruders 84 and 86 (sheath side –¾" single screw Killion extruder, core side –1.5" single screw Johnson extruder) and processed at a temperature of 250° C. The extruders each fed through a gear pump (Zenith) to control the individual flow rates of the materials, thereby controlling the composition of the fiber (percent sheath and percent core). The molten polymer was fed into the spin head holding the spinnerette pack 88 where the formation of the sheath-core fiber 92 takes place. The spinnerettes were held at a temperature ranging between 245 and 268° C., as set forth in Table 1. The fibers formed were air quenched 91 to solidify the filaments. A non-aqueous surface finish was applied to the fibers subsequently before being taken up by a feed roll and collected on a winder. The feed roll speed controlled the spin speed. This speed coupled with the individual flow rates of the sheath and core materials determined the final linear density of the fiber (denier) and the volume ratio of the fiber.

Figure 8:
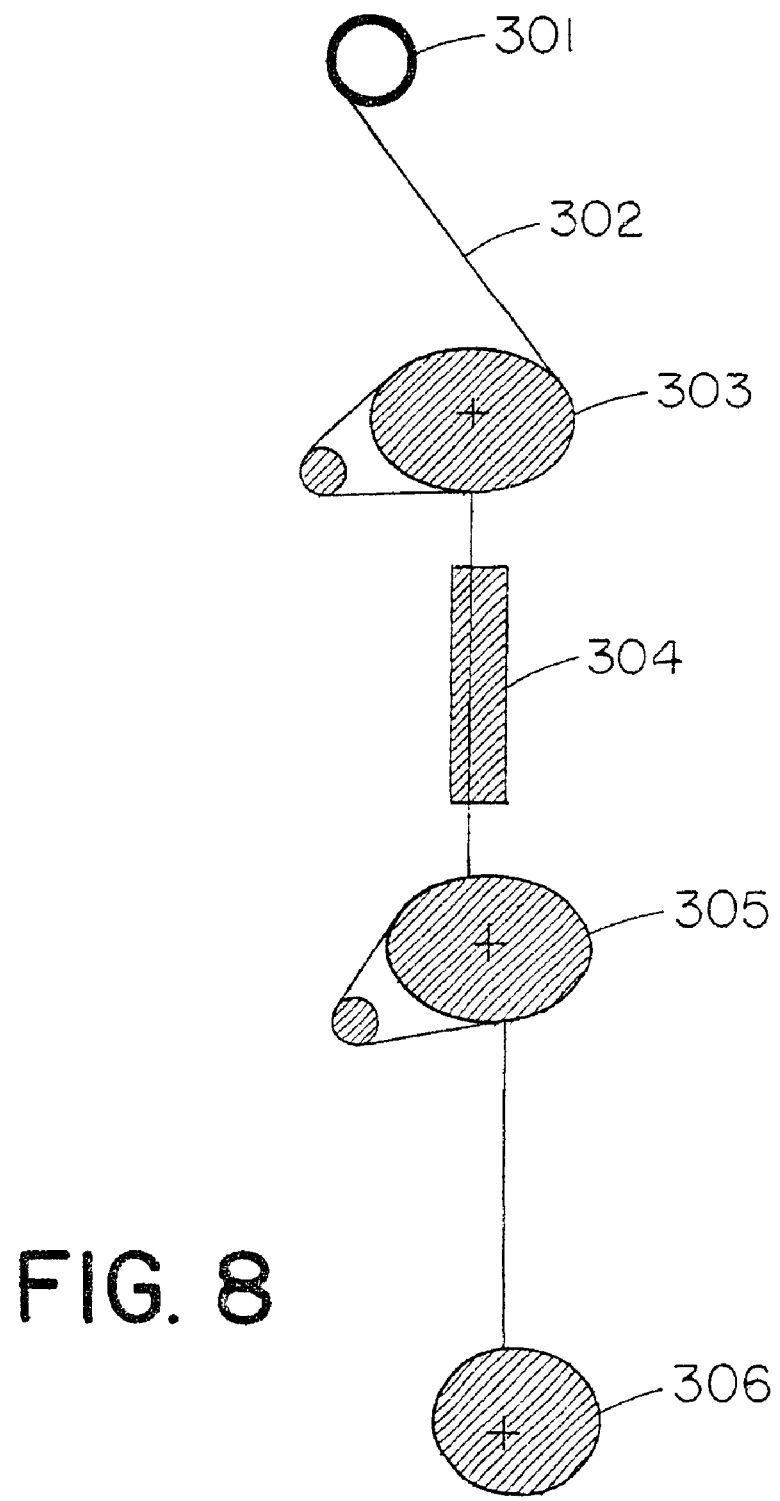
FIGS. 8 and 9 are schematics of the draw equipment which can be used in the manufacture of spun and drawn fibers.

The spun fiber was then subjected to drawing, illustrated in FIG. 8. The fiber 302 was taken from the bobbin 301 around a feed roll 303 and passed through a heated chamber 304 or a block onto a draw roll 305. The draw roll speed was "x" times faster than the feed roll speed which determined the draw ratio that the fiber was subjected to. The heated chamber/block transferred enough heat to fiber to initiate mobility of the polymer chains enabling efficient orientation. The drawn fiber was then collected on the winder 306.

The drawn fiber was then dried for 24 hours at room temperature under vacuum and stored under vacuum until needed.

The spinning conditions for generating 25/75, 50/50 and 75/25 PGA/PP and 50/50 PGA/PBT are listed below in Table 1. Clearly, a wide range of spin speed can be used to generate these bicomponent fibers. The process temperature varied from 245 to 268° C. Each threadline coming from the spinnerette consisted of 26 filaments. The number of threadlines can be varied depending on the size of the pack, throughput (mass flow rate of the molten polymers) and the spin speed at which these fibers are wound up. The spun and drawn fiber properties for one set of spin conditions for these different compositions are also listed in the Table. The different fibers have been drawn at various draw ratios which were determined by the spun elongation. The spun elongation was determined by the level of orientation in the fiber and can be changed by varying the spin speed and mass flow rate. Optical micrographs of the cross-section of some representative bicomponent fibers showed a controllable and reproducible method of making these bicomponent fibers.

TABLE 1

| Item | 3 | 7 | 6i | 38S | 9 | 10 | 15 |
|---|---|---|---|---|---|---|---|
| Sheath | PGA | PGA | PGA | PGA | PGA | PGA | PGA |
| Core | PP | PP | PP | PBT | PP | PP | PBT |
| Spin Speed (mpm) | 807.00 | 1342.00 | 900 | 948 | 1000 | 1000 | 464 |
| # of Threadlines | 1 | 1 | 1 | 2 | 2 | 2 | 2 |
| Process Temperature (° C.) | 250.50 | 249.5 | 250.6 | 255.6 | 263.5 | 263.9 | 268 |
| Core Flow rate (gm/min) | 3.73 | 11.05 | 2.30 | 7.00 | 8.4 | 4.4 | 9.1 |
| Sheath Flow rate (gm/min) | 5.65 | 5.65 | 9.08 | 7.60 | 11 | 13.2 | 8.5 |
| % Core (by volume) | 50 | 75 | 25 | 50 | 50 | 35 | 50 |
| % Sheath (by volume) | 50 | 25 | 75 | 50 | 50 | 65 | 50 |
| Spun Denier | 104 | 107 | 119 | 81 | 84 | 79 | 170 |
| Spun Elongation (%) | 232 | 265 | 237 | 183 | 199 | 216 | 373 |
| Spun Tenacity (gm/denier) | 1.69 | 1.99 | 1.57 | 2.09 | 1.5 | 2.2 | 1.1 |
| Finish Content (%) | 1.90 | 1.90 | 1.90 | 1.70 | 3.3 | 3.3 | 2.4 |
| Draw Temperature (° C.) | 88 | 88 | 88 | 120 | 88 | 88 | 120 |
| Draw Ratio | 2.7 | 2.9 | 2.9 | 2 | 2.04 | 2.00 | 3.48 |
| Drawn Denier | 39.17 | 36.74 | 45.69 | 41.14 | 43 | 39.83 | 50 |
| Drawn Elongation (%) | 27.925 | 29.56 | 26.62 | 33.29 | 48 | 48 | 35 |
| Drawn Tenacity (gm/denier) | 4.457 | 4.701 | 4.704 | 3.5 | 3.63 | 3.28 | 2.75 |

Differential scanning calorimetry (DSC) traces of a 50/50 PGA/PP spun and drawn fiber indicated the PP melt at 168° C. and the PGA melt at 217° C. The drawn fiber DSC also displayed the PP and PGA melting peaks; however, the shape of these peaks were altered. This reflected morphological changes in the PGA and PP materials when subjected to drawing. Drawing induced orientation of the polymer chains leading to a rearrangement of the crystalline morphology of both the materials. When the drawn fiber was taken up to 250° C. and cooled at 20° C./min to 50° C., there was a loss of the orientation and therefore the specific crystalline morphology in the materials. This became apparent when compared to the DSC trace of a quenched fiber without the orientation where the melting peaks were very broad compared to the sharper profiles seen for the drawn system.

The biological response of the bicomponent fibers (Items 3 and 38S), as evaluated by routine histopathologoy at various times in a rat subcutaneous implant, were strikingly different from that of a 100% non-resorbable polymer fiber of similar dimensions. The initial response seen during the first 7 to 10 days was typical of that seen at surgical wound sites. Numerous blood-derived macrophages were observed clearing fibrin and coagulated blood in and around fibers. At 14 days and beyond, non-resorbing permanent polymer fibers, e.g., polypropylene and polyester, provoked rapid formation of macrophage-derived multinuclear giant cells. These giant cells are thought to form from the fusion of macrophages. The giant cells persisted and grew in size in the permanent implant with increased time of implantation. Extracellular matrix production and associated fibroblast infiltration occurred. The bicomponent sheath/core fibers, however, produced an implant with equally numerous macrophages but the number of giant cells was diminished. At times after the sheath had been resorbed, the number of macrophages in and around the fibers declined. The tissue spaces between the fibers filled with extracellular matrix and small blood vessels in both permanent fibers and bicomponent sheath/core fibers, but this response was significantly more robust in the sheath/core bicomponent fiber.

In addition to providing a biopositive substrate for tissue growth regeneration, the bicomponent fiber also promotes tissue ingrowth via enhanced porosity as the sheath of the bicomponent fiber is resorbed. This porosity increase with implantation time can be modelled with the ANSI/AMI-vp20 (1994) "Method for determination for water permeability" vascular-prosthesis test. The PGA sheath of bicomponent fibers woven into plain-weave grafts was removed via graft immersion in ammonium hydroxide at pH 11.0 (+/−0.5) and 25° C. (+/−2° C.) shaker bath temperature for 16 hours. The graft was then dried and tested for porosity. The following data (in ml/cm$^2$/min at 120 mm pressure) was achieved:

TABLE 2

| Item | Porosity before sheath removal | Porosity after sheath removal |
| --- | --- | --- |
| 9 (50% PGA sheath 50% PP core) | 287 | 1742 |
| 15 (50% PGA sheath 50% PBT core) | 251 | 1674 |
| 10 (65% PGA sheath 35% PP core) | 564 | 3705 |

2) Spin-draw Process

Figure 9:
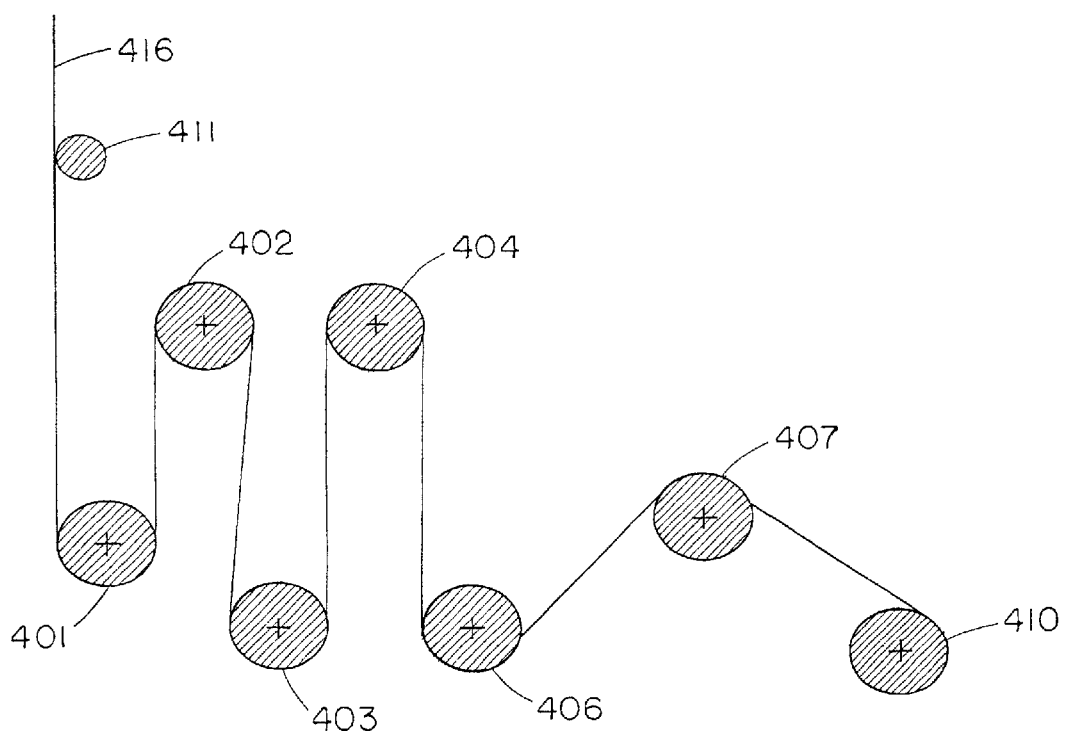

In a spin-draw process, the drawing step is added in line to the spinning process. FIG. 9 is a schematic of the process. The various godets are marked by 401 through 406. Godet 401 is the take-up godet and will determine the spin speed. The fiber 416 is contacted with a finish step 411 prior to being taken up by godet 401. The subsequent godets 402, 403 and 404 can be varied in manner where a desired draw ratio is achieved. Godet 405 is a heated roll where a temperature of 100–150° C. can be maintained to effectively begin the relaxation process for the drawn fibers 416. Godet 406 serves as the relax godet before the fibers are taken up on the winder 410.

Table 3 represents one specific condition from many possible variations of generating a 50/50 PGA/PP fiber by the spin-draw process. The main draw of ~2.5 is obtained between G1 and G3, with the relaxation occurring from G5 onwards. The hot roll, G5, is maintained at 130° C. The properties obtained by this process are comparable to that obtained by the two step process.

TABLE 3

| Item | 8 |
| --- | --- |
| Sheath | PGA |
| Core | PP |
| G1 (mpm) | 730.00 |
| G2 (mpm) | 770.00 |
| G3 (mpm) | 1808.00 |
| G4 (mpm) | 1808.00 |
| G5 (mpm | 1680.00 |
| G6 (mpm) | 1655.00 |
| Winder (mpm) | 1650.00 |
| # of Threadlines | 2 |
| Process Temperature (° C.) | 260.00 |
| PGA Flow rate (gm/min) | 9.50 |
| Core Flow rate (gm/min) | 6.10 |
| % Core (vol) | 50 |
| % Sheath (vol) | 50 |
| Denier | 38 |
| Elongation (%) | 31 |
| Tenacity (gm/denier) | 4.50 |
| Finish content (%) | 3.30 |

Equivalents

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. An implantable medical article comprising a textile-based structure said structure comprising at least one bicomponent fiber, wherein the bicomponent fiber comprises a first component formed from a resorbable material and a second component formed from a fiber-forming polymer which is non-resorbable, wherein the melting point of the second component is the same as or less than the melting point of the first component.

2. An implantable medical article comprising a textile-based structure said structure comprising at least one bicomponent fiber, wherein the bicomponent fiber comprises a first polymer component formed from a resorbable material and a second component formed from a fiber-forming polymer which is non-resorbable wherein the polymers in said first and second components are oriented.

3. The implantable medical article according to claim 2, wherein the first and the second component of the bicomponent fiber are simultaneously oriented during or subsequent to co-extrusion.

4. The implantable medical article according to claim 3, wherein said second component is disposed within said first component.

5. The implantable medical article according to claim 3 wherein said second component is selected from the group consisting of polyesters, polyamides, polyolefins, and segmented polyurethanes.

6. The implantable medical article according to claim 3 wherein said second component is selected from the group consisting of polypropylene, polyethylene, polybutyleneterephthalate and polyhexamethyleneterephthalate.

7. The implantable medical article according to claim 3, wherein said first component induces a biopositive response in vivo.

8. The implantable medical article according to claim 3 wherein said first component is selected from the group consisting of polyglycolides, polydioxanones, polyhydroxyalkanoates, polylactides, alginates, chitosans, collagens, polyalkylene oxalates, polyanhydrides, poly(glycolide-co-trimethylene carbonate), polyesteramides, and polydepsipeptides.

9. The implantable medical article according to claim 3 wherein said first component is a polyglycolide polymer or a polyglycolide-polylactide copolymer.

10. The implantable medical article according to claim 3 wherein at least one of said components further comprises at least one pharmaceutical agent.

11. The implantable medical article according to claim 3, wherein said first component is substantially free of cracks or delamination.

12. The implantable medical article according to claim 3 wherein said first component possesses a substantially uniform thickness along the axis of the fiber.

13. The implantable medical article according to claim 3 wherein a volume ratio of said first component to said second component is from about 1:10 to about 10:1.

14. The implantable medical article according to claim 3 wherein the first polymer component is a fiber-forming polymer.

15. The implantable medical article according to claim 3, wherein the volume ratio of said first component to said second component is substantially the same along the length of the fiber.

16. An implantable medical article comprising a textile-based structure said structure comprising at least one bicomponent fiber, wherein the bicomponent fiber is manufactured by coextrusion of a first resorbable polymer and a second fiber-forming polymer which is non-resorbable under conditions which form a bicomponent fiber wherein the second fiber-forming polymer is continuously disposed within the first polymer at a substantially constant volume ratio of said first polymer to said second polymer along the length of the bicomponent fiber.

17. An implantable medical article comprising a textile-based structure said structure comprising a bicomponent fiber produced by a process comprising simultaneously melt-extruding from a spinnerette in a sheath-core filament configuration, a first polymer component formed from a resorbable material and a second component formed from a fiber-forming polymer which is non-resorbable.

18. An implantable medical article comprising a textile-based structure said structure comprising a bicomponent fiber, wherein the bicomponent fiber comprises a first polymer component formed from a resorbable material and a second component formed from a fiber-forming polymer which is non-resorbable, wherein said bicomponent fiber is produced by a process comprising the steps of:

(a) simultaneously solution-spinning from a spinnerette in a sheath-core filament configuration, a first solution comprising a first solvent and the first polymer component and a second solution comprising a second solvent and the second component, thereby forming a prefilament; and (b) removing said first and second solvents from said prefilament thereby forming a bicomponent fiber wherein said second component is substantially disposed within said first component.

* * * * *